Oct. 31, 1961 E. G. FISHER Plant Pat. 2,100
ROSE PLANT
Filed Sept. 2, 1960
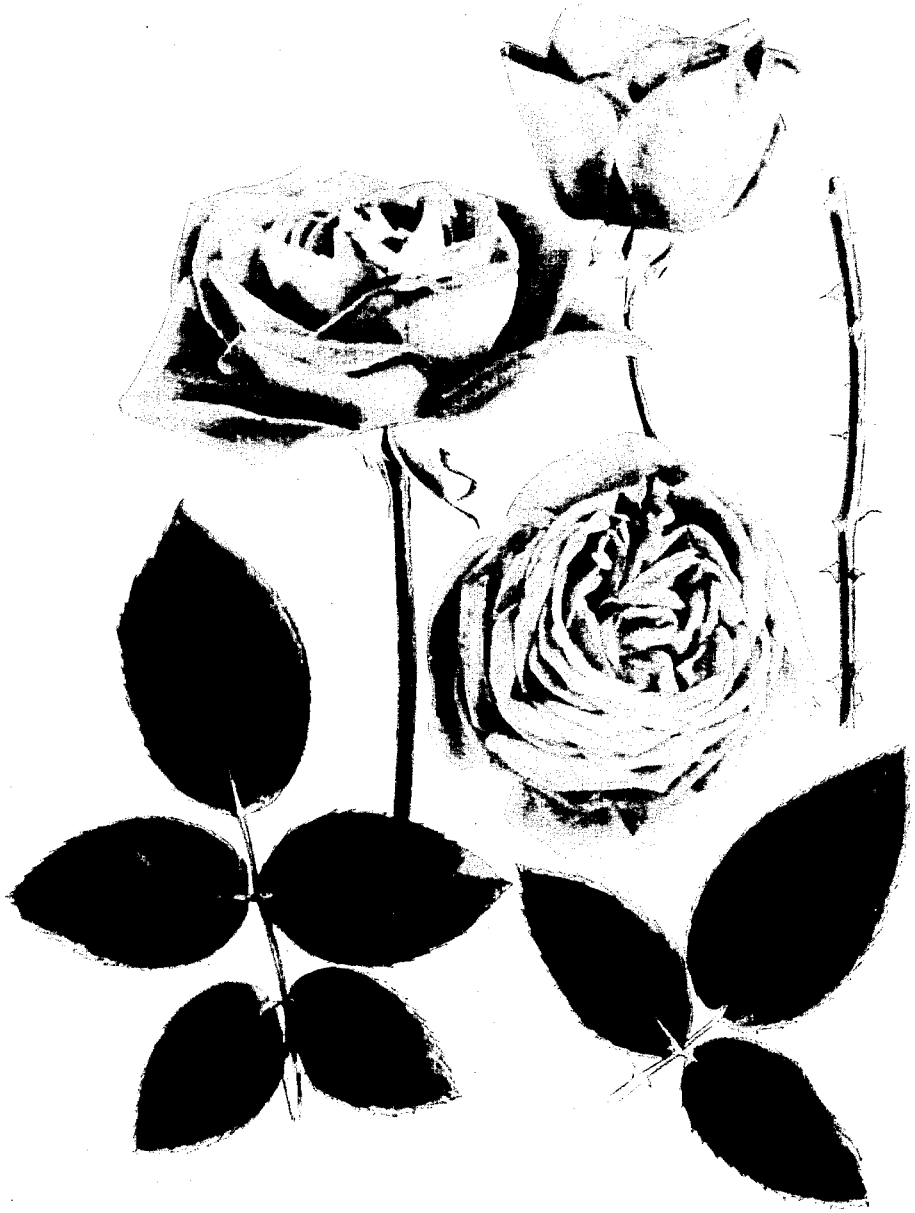
Esther Gladys Fisher,
Inventor
Smucker & Mathis
Attorneys.

United States Patent Office

Plant Pat. 2,100
Patented Oct. 31, 1961

2,100
ROSE PLANT

Esther Gladys Fisher, Woburn, Mass., assignor to Arnold-Fisher Company, Woburn, Mass., a corporation of Massachusetts Filed Sept. 2, 1960, Ser. No. 53,860
1 Claim. (Cl. 47—61)

This invention relates to a new and distinct variety of rose plant of the hybrid tea class, which was originated by me by crossing a greenhouse-type rose with a garden-type rose.

The primary objective of this breeding was to create a red greenhouse rose of clear and unfading color on a plant which would produce blooms continuously throughout the year, of a shape and size suitable for the florist trade.

In achieving this objective, I used, in making the cross, a blend of the female parent "Happiness," a greenhouse rose, with the male parent "New Yorker," a garden rose. The resulting seedling of these parents has the shape and red color substantially similar to "New Yorker" and the continuous bloom, keeping and shipping qualities of "Happiness," as well as the long pointed bud of "Happiness," which is highly desirable in a greenhouse rose. The plant has the necessary characteristics for forcing, which is the customary practice in the greenhouse trade. Many firm textured petals are a requirement in roses offered to the public, since frequent handling is required before the roses reach the ultimate customer.

A sexual reproduction of my new variety by budding, as performed by me in greenhouses in Woburn, Massachusetts, shows that the aforementioned characteristics and distinctions come true to form and are established and transmitted through succeeding propagation.

The accompanying drawing shows typical specimens of the flowers and foliage of my new variety in different stages of development and as depicted in color as nearly true as is reasonably possible to make the same in a color illustration of this character.

The following is a detailed description of my new variety with color terminology in accordance with the color chart of the Royal Horticultural Society referred to as "R.H.S." and the Nickerson Munsel Hue Fan referred to as "N.M.H."

Type: Hardy; upright; indoor; seedling; for cut flowers.
Class: Hybrid tea.
Breeding: Seedling.
*Seed parent.*—Happiness (Plant Patent No. 911).
*Male parent.*—New Yorker (Plant Patent No. 823).

*Flower*

Locality where grown: Greenhouses in Woburn, Massachusetts.
Flowers borne: Single on medium and long stems.
Quantity of bloom: Blooms continuously throughout the year. From Sept. 1 to April 10 on test plant, had eighteen blooms.
Fragrance: Moderate clove scent.
Bud:
*Peduncle.*—3 to 3½ inches long; heavy; erect. Moderate yellow green 2.56Y 5/6 N.M.H. Tiny thorns on peduncle are dark red 5R 3/7 N.M.H.
*Before calyx breaks.* — Size — medium. Form—pointed high centered. Sepal—length 1⅝ inches. Outside color—moderate yellow green 56Y 5/6 N.M.H.
*As calyx breaks.*—Inside sepal color has white streaks from the base extending two thirds towards tip. Some sepals are smooth edged—others foliaceous.
*As first petal opens.*—From base to tip size 2¼ inches. Form—round. Color outside—current red 821 R.H.S. Where petal attaches to calyx a small area of strong yellow 5Y 7/10 N.M.H. Inside color—cardinal red 822 R.H.S. Upper half of outer petal has shadings of black.

Bloom:
*Size when fully open.*—5 to 5½ inches.
*Petalage.*—Double, forty to fifty-five petals arranged regularly.
*Form.*—High centered opening to somewhat cupped flower, until fully open when it is a full well rounded flower with petals covering stamens.
Petals: Firm texture; outside—satiny; inside—velvety. Shape—roundly ovate with minute point at center.

This description of a newly opened flower was made from a rose grown in greenhouse at Woburn, Massachusetts in April 1960.

Flower longevity: Slowly opens to a long lasting flower. Fades very little.

*Reproductive organs*

Stamens: Many arranged regularly around pistil, same height as pistil.
Filaments: Many—length 5/16 inch. Color—moderate red 25R 4/10 N.M.H. with base moderate pink 5R 8/6 N.M.H.
Anthers: Length 3/16 inch long and pointed. Color—moderate orange yellow 10YR 8/10 N.M.H.—some edged with red.
Pollen: Moderate—gold.
Pistils: Uneven, 3/16 to 5/16 inch.
Styles: Moderate red 25R 4/10 N.M.H.
Stigma: Strong yellow 2.5Y 7/10 N.M.H.
Ovaries: Small—3/16 to 5/16 inch in depth 7/16 inch in width. Color—strong yellow green 7.56Y 6/10 N.M.H.
Hips: The following is an analysis of a seed pod developed from a cross of this seedling as female parent and "Best Wishes" as the male parent. Examined on May 2, 1960. Color: Moderate yellow, size—one inch in diameter across top; ¾ inch measured from base to rim of top. All seeds exposed on top with none in pod itself.
Seeds: 27 seeds of large size, round at top and pointed at bottom. Color—light beige with a few tinted pink on top round part.

*Plant*

Foliage:
*Leaves.*—Compound of 5 and 7 leaflets; moderately heavy; dull with slight sheen.
*Leaflets.*—Shape—oval with apex acute; margin simple serrate; veins noticeable.
*Colors.*—Mature upper surface—dark grayish green 106Y 3/2 N.M.H. Under surface—spinach green 0960/2 R.H.S.
*Rachis.* — Upper side grooved — strong, mostly smooth, but occasionally 2 to 3 thorns.
*Stipules.*—½ inch long by about ⅛ inch wide with points sometimes coming out at right angles or less.
*Disease.*—Resistance comparable to the average variety grown in greenhouses.
Growth:
*Habit.*—Upright, robust growing to about 7 to 8 feet in greenhouse.
*Growth.*—Free and strong, breaks easily into new growth.
*Canes.*—Medium heavy.
*Main stems.*—Very strong, glossy. Color—moderate olive green 2.56Y 4/3 N.M.H. with overlay of reddish bronze tint.
*Thorns.*—Several; dark red 5R 3/7 N.M.H. at base; tips shade to green. Thorns are both and little.

*New growth.*—Color: Leaf upper surface—green overlaid with red giving a bronze effect. Under surface is red with an underlay of green.

I claim:

A new and distinct variety of rose plant of the hybrid tea class, substantially as herein shown and described, characterized particularly as to novelty by the unique combination of medium to long flower stems, a long pointed bud form, a distinctive Current Red general color tonality, and long lasting qualities of the flower.

No references cited.